(12) United States Patent
Baril

(10) Patent No.: US 12,350,828 B2
(45) Date of Patent: Jul. 8, 2025

(54) SURGICAL ROBOTIC SYSTEMS INCLUDING SURGICAL INSTRUMENTS WITH ARTICULATION

(71) Applicant: Covidien LP, Mansfield, MA (US)

(72) Inventor: Jacob Baril, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 651 days.

(21) Appl. No.: 17/764,226

(22) PCT Filed: Dec. 4, 2020

(86) PCT No.: PCT/US2020/063225
§ 371 (c)(1),
(2) Date: Mar. 28, 2022

(87) PCT Pub. No.: WO2021/126545
PCT Pub. Date: Jun. 4, 2021

(65) Prior Publication Data
US 2022/0371180 A1    Nov. 24, 2022

Related U.S. Application Data

(60) Provisional application No. 62/948,414, filed on Dec. 16, 2019.

(51) Int. Cl.
*B25J 9/10* (2006.01)
*B25J 17/02* (2006.01)
*A61B 34/30* (2016.01)

(52) U.S. Cl.
CPC ............. *B25J 9/102* (2013.01); *B25J 17/025* (2013.01); *A61B 2034/306* (2016.02)

(58) Field of Classification Search
CPC ......... B25J 9/102; B25J 17/025; A61B 1/008; A61B 2034/301; A61B 2034/302; A61B 2034/303; A61B 2034/305
See application file for complete search history.

(56) References Cited

U.S. PATENT DOCUMENTS 6,132,368 A    10/2000   Cooper
6,206,903 B1    3/2001   Ramans
(Continued)

FOREIGN PATENT DOCUMENTS

| EP | 2364825 A1 * | 9/2011 | ............. A61B 34/30 |
| WO | 2012006306 A2 | 1/2012 | |
| WO | 2015088655 A1 | 6/2015 | |

OTHER PUBLICATIONS

International Search Report mailed Mar. 3, 2021 and Written Opinion completed Feb. 23, 2021 corresponding to counterpart Int'l Patent Application PCT/US2020/063225.

*Primary Examiner* — Bobby Rushing, Jr.
(74) *Attorney, Agent, or Firm* — Carter, DeLuca & Farrell LLP

(57) ABSTRACT

A surgical instrument includes a shaft, an end effector, and an articulation mechanism. The end effector is movable between a first position where the end effector is aligned with a longitudinal axis of the shaft, and a second position where the end effector is disposed at an angled relative to the longitudinal axis. The articulation mechanism includes a proximal gear disposed in mechanical cooperation with the shaft, a distal gear disposed in mechanical cooperation with the end effector, a first lateral gear disposed in contact with the proximal gear and the distal gear, and a second lateral gear disposed in contact with the proximal gear and the distal gear.

19 Claims, 13 Drawing Sheets

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,353,440 B2 * | 1/2013 | Whitman ............ A61B 17/068 227/19 |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |

(56) References Cited

U.S. PATENT DOCUMENTS

| | | |
|---|---|---|
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,220,508 B2 | 12/2015 | Dannaher |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Arkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Arkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,220,522 B2 * | 3/2019 | Rockrohr ......... A61B 17/00234 |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | Mcdonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |

(56) References Cited

U.S. PATENT DOCUMENTS

| | | | |
|---|---|---|---|
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2005/0177138 A1 | 8/2005 | Dubrovsky |
| 2014/0083233 A1* | 3/2014 | Mamba ............... B25J 9/102 901/26 |
| 2014/0114293 A1 | 4/2014 | Jeong et al. |

\* cited by examiner

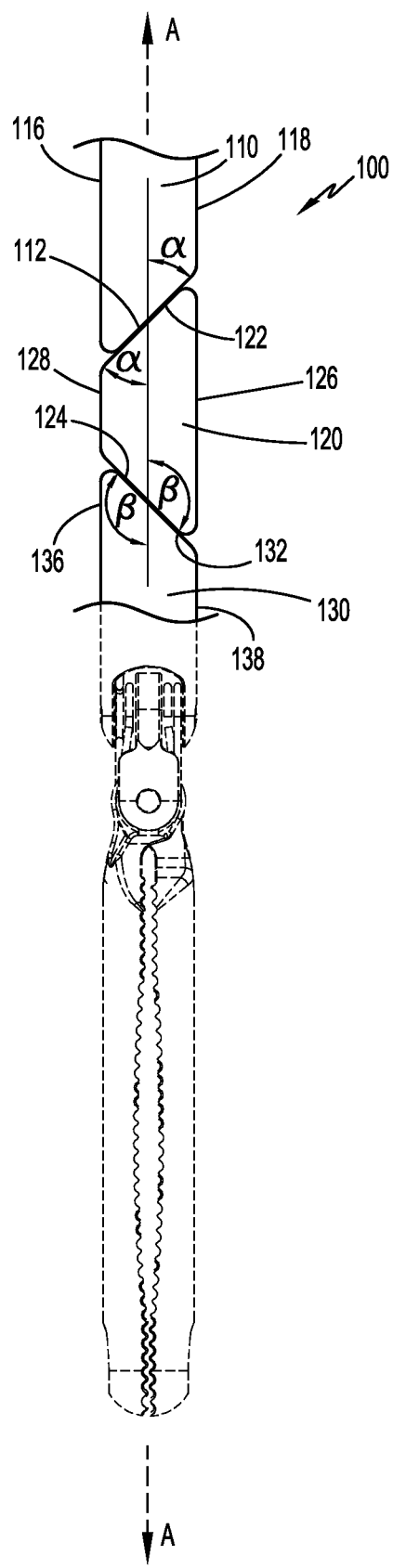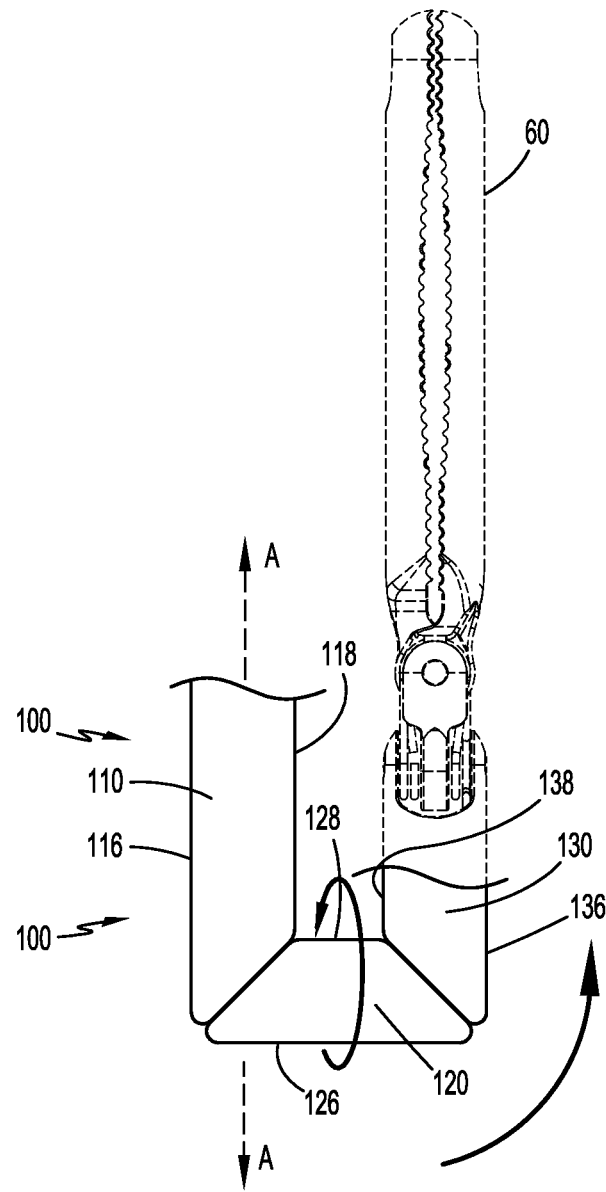
FIG. 3
FIG. 4

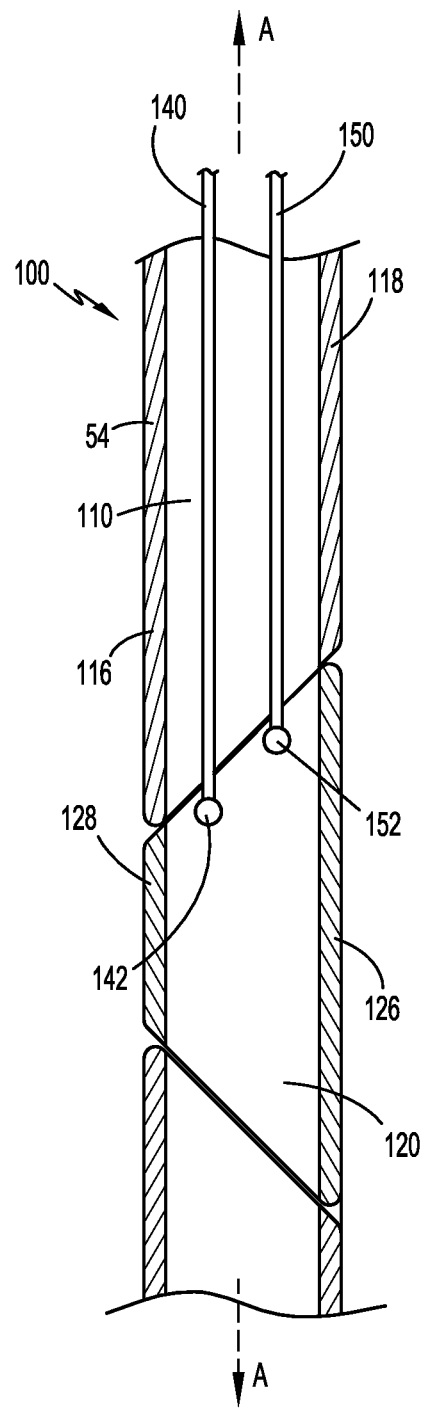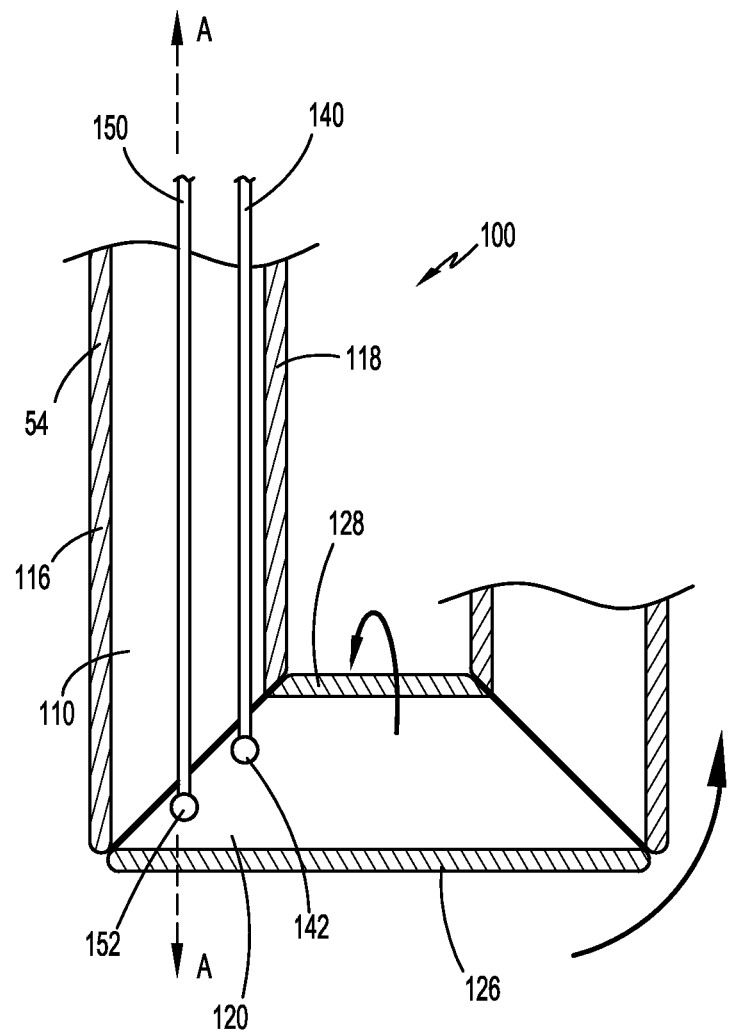
FIG. 5
FIG. 6

SURGICAL ROBOTIC SYSTEMS INCLUDING SURGICAL INSTRUMENTS WITH ARTICULATION

CROSS-REFERENCE TO RELATED APPLICATIONS

The present application is a U.S. National Stage Application filed under 35 U.S.C. § 371(a) claiming the benefit of and priority to International Patent Application No. PCT/US2020/063225, filed Dec. 4, 2020, which claims the benefit of and priority to U.S. Provisional Patent Application Ser. No. 62/948,414, filed Dec. 16, 2019, the entire disclosures of each of which being incorporated by reference herein.

BACKGROUND

Surgical robotic systems are currently being used in minimally invasive medical procedures. During some surgical robotic procedures, it may be helpful for an end effector of a surgical instrument to have the ability to articulate and/or rotate.

SUMMARY

The present disclosure relates to a surgical instrument including a shaft, an end effector, and an articulation mechanism. The shaft defines a longitudinal axis. The end effector is disposed adjacent a distal end of the shaft and defining a respective longitudinal axis. The articulation mechanism is disposed in mechanical cooperation with the shaft and the end effector, and is configured to allow the end effector to move between a first position where at least a portion of the end effector defining the longitudinal axis thereof is aligned with the longitudinal axis and a second position where the portion of the end effector defining the longitudinal axis thereof is disposed at an angle relative to the longitudinal axis. The articulation mechanism includes a proximal gear disposed in mechanical cooperation with the shaft, a distal gear disposed in mechanical cooperation with the end effector, a first lateral gear disposed in contact with the proximal gear and the distal gear, and a second lateral gear disposed in contact with the proximal gear and the distal gear.

In disclosed embodiments, the first lateral gear has a smaller diameter than the second lateral gear.

It is also disclosed that the first lateral gear is disposed on a first lateral side of the longitudinal axis of the shaft, and the second lateral gear is disposed on a second lateral side of the longitudinal axis of the shaft.

It is further disclosed that the proximal gear is a bevel gear, and that the distal gear is a bevel gear. In embodiments, the first lateral gear is a bevel gear, and the second lateral gear is a bevel gear.

It is still further disclosed that the articulation mechanism of the surgical instrument includes a tube extending through a central aperture of the proximal gear and through a central aperture of the distal gear. It is disclosed that a proximal end of the tube includes a flared portion configured to engage an angled portion of the proximal gear, and a distal end of the tube includes a flared portion configured to engage an angled portion of the distal gear.

In disclosed embodiments, the tube includes a first lateral projection for rotatably supporting the first lateral gear, and a second lateral projection for rotatably supporting the second lateral gear. It is disclosed that the first lateral projection and the second lateral projection extend from the same longitudinal position of the tube.

It is further disclosed that when the end effector is in the first position, a narrow portion of the proximal gear is longitudinally aligned with a narrow portion of the distal gear, and a wide portion of the proximal gear is longitudinally aligned with a wide portion of the distal gear. Additionally, when the end effector is in the second position, the narrow portion of the proximal gear is longitudinally aligned with the wide portion of the distal gear, and the wide portion of the proximal gear is longitudinally aligned with the narrow portion of the distal gear.

It is also disclosed that the proximal gear of the surgical instrument is configured to be rotated by a robot.

The present disclosure also relates to an articulation mechanism for use with a surgical instrument. The articulation mechanism includes a proximal bevel gear disposed in mechanical cooperation with a shaft of the surgical instrument, a distal bevel gear disposed in mechanical cooperation with an end effector of the surgical instrument, a first lateral gear disposed in contact with the proximal bevel gear and the distal bevel gear, and a second lateral gear disposed in contact with the proximal bevel gear and the distal bevel gear. The first lateral gear has a smaller diameter than the second lateral gear.

In disclosed embodiments, the first lateral gear is a bevel gear, the second lateral gear is a bevel gear, and the first lateral gear is free from contact with the second lateral gear.

In embodiments, the articulation mechanism includes a tube extending through a central aperture of the proximal gear and through a central aperture of the distal gear. The tube is configured to prevent longitudinal movement of the distal bevel gear relative to the proximal bevel gear.

It is further disclosed that a proximal end of the tube includes a flared portion configured to rotatably engage an angled portion of the proximal gear, and a distal end of the tube includes a flared portion configured to rotatably engage an angled portion of the distal gear.

It is also disclosed that the tube includes a first lateral projection for rotatably supporting the first lateral gear, and a second lateral projection for rotatably supporting the second lateral gear. In embodiments, the first lateral projection and the second lateral projection extend from the same longitudinal position of the tube.

BRIEF DESCRIPTION OF THE DRAWINGS

Embodiments of the present disclosure are described herein with reference to the accompanying drawings, wherein:

FIG. 3 is a side view of the distal end of the surgical instrument of FIGS. 1 and 2 shown in a non-articulated orientation;

FIG. 4 is a side view of the distal end of the surgical instrument of FIGS. 1 and 2 shown in an articulated orientation;

FIG. 5 is a side, cross-sectional view of a portion of the surgical instrument taken along section line 5-5 in FIG. 2, and shown in a non-articulated orientation;

FIG. 6 is a side, cross-sectional view of the portion of the surgical instrument shown in FIG. 5, and shown in an articulated orientation;

DETAILED DESCRIPTION

Figure 1:
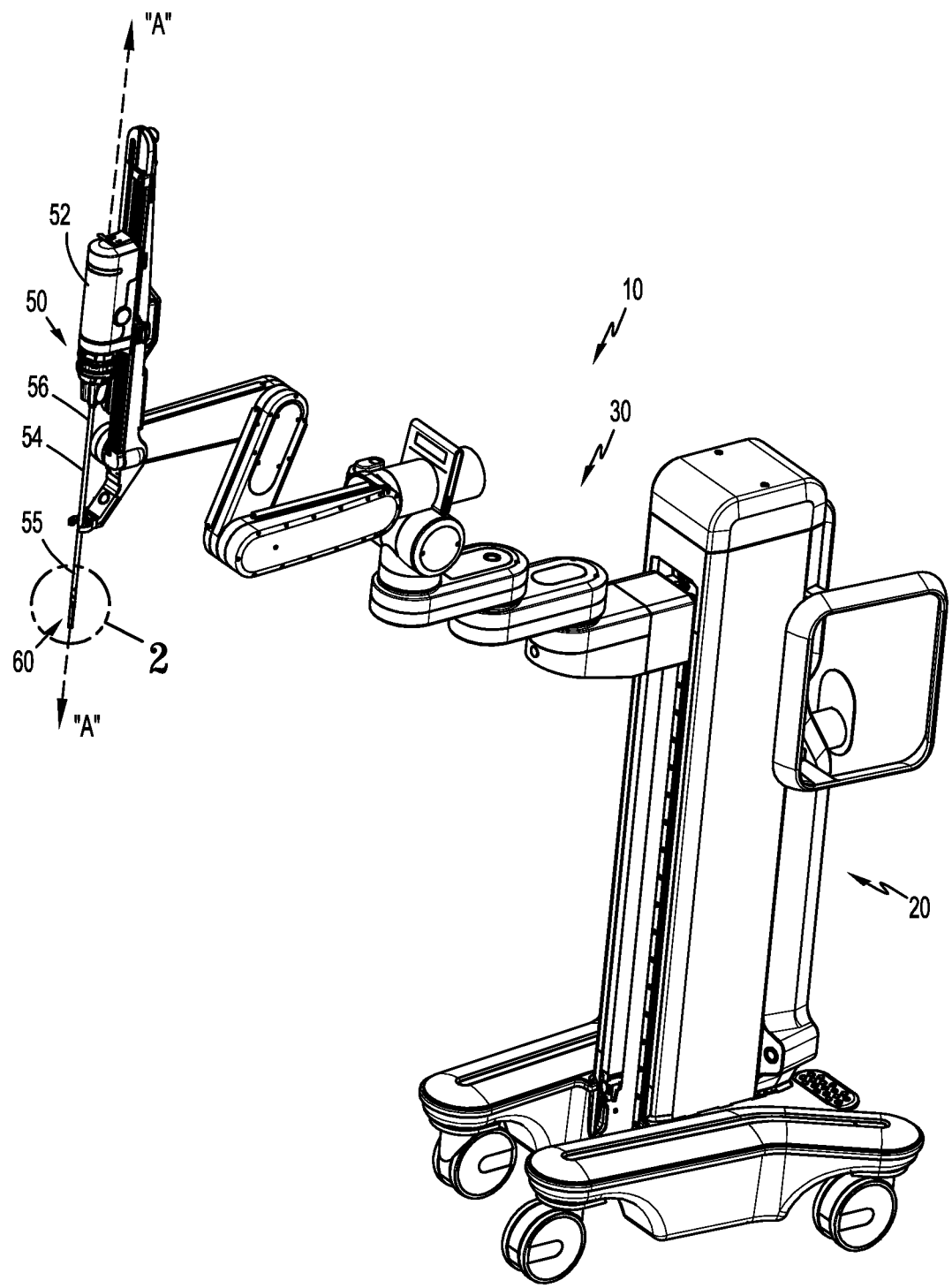
FIG. 1 is a schematic illustration of a component of a surgical robotic system including a surgical robotic cart, a surgical robotic arm, and a surgical instrument according to the present disclosure.
Figure 2:
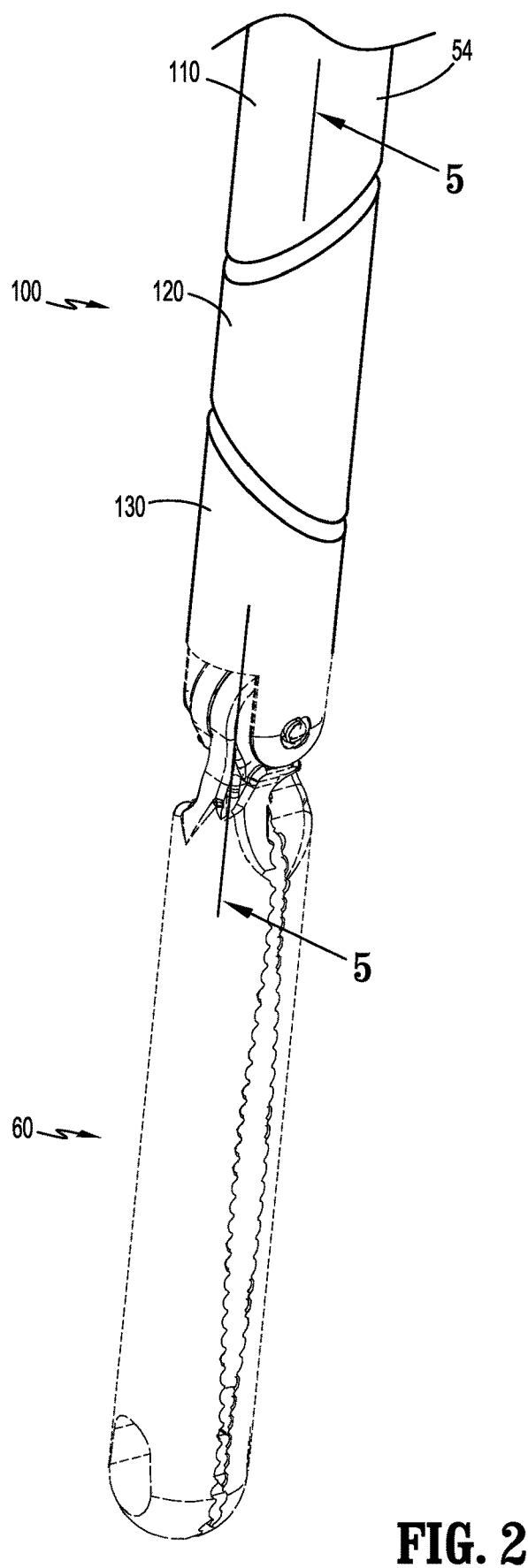
FIG. 2 is an enlarged view of the area detailed in FIG. 1 illustrating a distal end of the surgical instrument having a first type of articulation mechanism.
Figure 7:
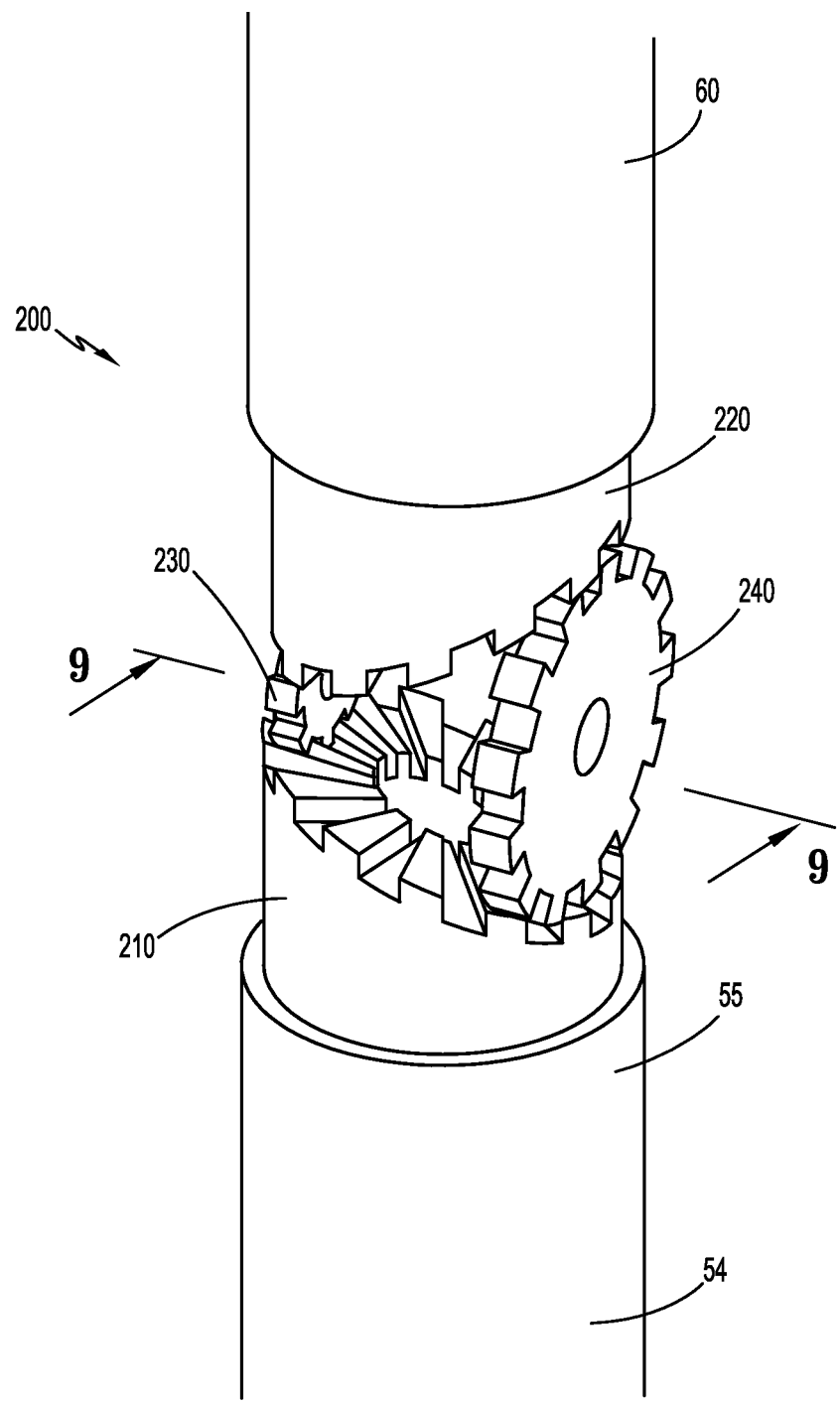
FIG. 7 is a perspective view of a portion of a surgical instrument for use with the surgical robotic cart of FIG. 1 shown with a second type of articulation mechanism in accordance with the present disclosure.

Persons skilled in the art will understand that the surgical robotic instruments or systems specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the described embodiments. Accordingly, the disclosure is not to be limited by what has been particularly shown and described, except as indicated by the appended claims.

Embodiments of the presently disclosed surgical robotic instruments are described in detail with reference to the drawings, in which like reference numerals designate identical or corresponding elements in each of the several views. As used herein the term "distal" refers to the portion of the surgical robotic instrument or portion thereof that is closer to the patient, while the term "proximal" refers to the portion that is farther from the patient.

As will be described in detail below, the present disclosure is directed to surgical instruments or systems (e.g., robotic surgical instruments or systems) including an end effector having the ability to articulate and/or rotate. In robotic surgery, for example, surgical instruments having the ability to articulate and/or rotate may be helpful to access particular surgical locations and/or in connection with surgical instruments having a relatively small diameter (e.g., about 5 mm) to help enable a surgical robot to apply relatively large loads or force without unnecessary straining the user or surgical robot. The present disclosure details various embodiments of articulation mechanisms of a surgical instrument to allow for articulation and/or rotation of its end effector, while maintaining the ability to be controlled by a surgical robot.

With reference to FIG. 1, a surgical robotic system 10 includes a surgical robotic cart 20, a robotic arm 30 mounted to the surgical robotic cart 20, and a surgical instrument 50 removably coupled to the robotic arm 30. The surgical instrument 50 is configured for use during minimally invasive surgical procedures. In embodiments, the surgical instrument 50 may be configured for open surgical procedures. Additionally, while not explicitly shown in the accompanying figures, the surgical robotic system 10 may also include a control tower, a surgical console, more than one robotic arm, and more than one surgical instrument. As in known in the art, the control tower and/or surgical console are able to remotely control various aspects of the surgical robotic system 10, such as the positioning of the robotic arm 30 relative to the surgical robotic cart 20, positioning of the surgical instrument 50 relative to the robotic arm 30, and actuation of the surgical instrument 50.

In addition to the various positioning options of the surgical instrument 50 relative to the surgical robotic cart 20, the surgical instrument 50 also includes an end effector 60 at its distal end, which is positionable at different orientations relative to a proximal portion 52 (e.g. handle) of the surgical instrument 50. In particular, the surgical instrument 50 includes an articulation mechanism configured to allow the end effector 60 to move between a first, non-articulated orientation where the end effector 60 is aligned with a longitudinal axis "A-A" defined by a shaft 54 of the surgical instrument 50, and a second, articulated orientation where the end effector 60 is disposed at an angle relative to and/or displaced from alignment with the longitudinal axis "A-A." In addition to having the ability to be articulated in this regard, the surgical instrument 50 can also be remotely controlled to perform other surgical functions such as, approximating its jaw members, ejecting fasteners into tissue, severing tissue, applying energy to tissue, etc., for instance.

With reference to FIGS. 2-6, a first embodiment of an articulation mechanism 100 is shown and is generally indicated by reference character 100. The articulation mechanism 100 is disposed near a distal end of the shaft 54 of the surgical instrument 50, and proximally of the end effector

60. Articulation mechanism 100 is configured as a stove pipe arrangement to allow the end effector 60 to move relative to the proximal portion 52 of the shaft 54 to help improve the versatility of the surgical instrument 50, for example. The articulation mechanism 100 includes a first link 110, a second link 120, and a third link 130. The first link 110, which may be formed on a portion of the shaft 54, is rotatably coupled to the second link 120. The second link 120 is rotatably coupled to the third link 130, which may be formed on a portion of the end effector 60.

With particular reference to FIG. 3, a distal end 112 of the first link 110 is disposed at an angle α relative to the longitudinal axis "A-A" defined by the shaft 54. A proximal end 122 of the second link 120 is also disposed at the angle α relative to the longitudinal axis "A-A." A distal end 124 of the second link 120 is disposed at an angle β relative to the longitudinal axis "A-A," and a proximal end 132 of the third link 130 is also disposed at the angle β relative to the longitudinal axis "A-A." As is evident from the description below, the actual angles of α and β will help determine the amount of articulation of the end effector 60 relative to the shaft 54. While the angles of α and β can be any suitable angle, it is envisioned that angle α and β are between about 25° and about 75°. Additionally, angle α may be greater than, equal to, or less than angle β without departing from the scope of the present disclosure.

Further, and with continued reference to FIG. 3, the angled end(s) of the first link 110, the second link 120 and the third link 130 result in each link having a longer side and a shorter side. That is, first link 110 includes a longer side 116 and a shorter side 118, second link 120 includes a longer side 126 and a shorter side 128, and third link 130 includes a longer side 136 and a shorter side 138. As shown in FIG. 3, when the end effector 60 is in the non-articulated position, the longer side 116 of the first link 110 is aligned or substantially aligned with the shorter side 128 of the second link 120 and with the longer side 136 of the third link 130. Additionally, in this position, the shorter side 118 of the first link 110 is aligned or substantially aligned with the longer side 126 of the second link 120 and with the shorter side 138 of the third link 130.

Referring now to FIGS. 5 and 6, articulation mechanism 100 also includes a first rod 140 and a second rod 150. A portion of the first rod 140 extends at least partially through the shaft 54 of the surgical instrument 50 and through the first link 110, and a distal end 142 of the first rod 140 is disposed within the second link 120 on a first lateral side of the longitudinal axis "A-A." The first rod 140 is longitudinally translatable relative to at least a portion of the shaft 54 and the first link 110, while the distal end 142 of the first rod 140 is longitudinally fixed to the second link 120. A portion of the second rod 150 extends at least partially through the shaft 54 of the surgical instrument 50 and through the first link 110, and a distal end 152 of the second rod 150 is disposed within the second link 120 on a second lateral side of the longitudinal axis "A-A." The second rod 150 is longitudinally translatable relative to at least a portion of the shaft 54 and the first link 110, while the distal end 152 of the second rod 150 is longitudinally fixed to the second link 120.

Proximal ends of the first rod 140 and the second rod 150 are disposed at a suitable location proximally of the first link 110, e.g., within an adapter, within the shaft 54, or within the proximal portion 52 of the surgical instrument 50. Additionally, the proximal ends of the first rod 140 and the second rod 150 are able to be controlled wirelessly to longitudinally translate the first rod 140 and the second rod 150 relative to the shaft 54 of the surgical instrument 50, and/or to rotate the first rod 140 and the second rod 150 about the longitudinal axis "A-A." Such wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

In use, the first rod 140 and the second rod 150 are manipulated to cause a desired articulation of the end effector 60. For instance, and with particular reference to FIGS. 5-6, the first rod 140 and the second rod 150 can both be moved distally causing the second link 120 to move away from the first link 110. Next, or at the same time, the first rod 140 and the second 150 can be rotated (e.g., about 180°) about the longitudinal axis "A-A" and relative to the first link 110, followed by the first rod 140 and the second rod 150 (and thereby the second link 120) moving proximally such that the second link 120 is back into engagement with the first link 110. This manipulation of the first rod 140 and the second rod 150 causes the second link 120 to articulate relative to the first link 110. That is, as shown in FIG. 6, in this position where the end effector 60 is in an articulated position, the longer side 116 of the first link 110 is aligned or substantially aligned with the longer side 126 of the second link 120. Additionally, in this position, the shorter side 118 of the first link 110 is aligned or substantially aligned with the shorter side 128 of the second link 120.

With continued reference to FIGS. 2-6, it is further disclosed that the first link 110 and the third link 130 are rotationally fixed relative to each other. For instance, a cable or a rod (not explicitly shown) may be rotationally fixed to the first link 110, extend through a central channel in the second link 120, and be rotationally fixed to the third link 130. This connection prevents the third link 130 from rotating relative to the first link 110, and could also keep the distal end 112 of the first link 110 in tension with the proximal end 122 of the second link 120, and keep the distal end 124 of the second link 120 in tension with the proximal end 132 of the third link 130 thereby providing additional robustness to the articulation mechanism 100.

In disclosed embodiments, the first rod 140 and the second rod 150 are biased (e.g., spring-biased) proximally to help maintain the desired articulation, for instance.

Additionally, the surgical instrument 50 including the first articulation mechanism 100 has improved access to target tissue by having the ability to rotate. That is, the proximal portion 56 of the shaft 54 of the surgical instrument 50 can rotate about itself (e.g., the longitudinal axis "A-A"), thereby causing the end effector 60 (either in an articulated position or a non-articulated position) to rotate about the longitudinal axis "A-A."

With reference to FIGS. 7-11, a second embodiment of an articulation mechanism is shown and is generally indicated by reference character 200. The articulation mechanism 200 is disposed near a distal end 55 of the shaft 54 of the surgical instrument 50, and proximally of or in engagement with the end effector 60. Articulation mechanism 200 is configured to allow the end effector 60 to move relative to the proximal portion 56 of the shaft 54 to help improve the versatility of the surgical instrument 50, for example. The articulation mechanism 200 includes a proximal gear 210, a distal gear 220, a first lateral gear 230 and a second lateral gear 240. The proximal gear 210 is formed on or otherwise engaged with the distal end 55 of the shaft 54, and the distal gear 220 is formed on or otherwise engaged with a proximal end of the end effector 60. The first lateral gear 230 and the second lateral gear 240 are disposed between the proximal gear 210 and the distal gear 220.

More particularly, the proximal gear 210 is a bevel gear, the distal gear 220 is a bevel gear, and the first lateral gear 230 is smaller than the second lateral gear 240. Both of the first lateral gear 230 and the second lateral gear 240 engage the proximal gear 210 and the distal gear 220. Additionally, the first lateral gear 230 and the second lateral gear 240 are beveled such that they mesh with the proximal gear 210 and the distal gear 220.

Figure 9:
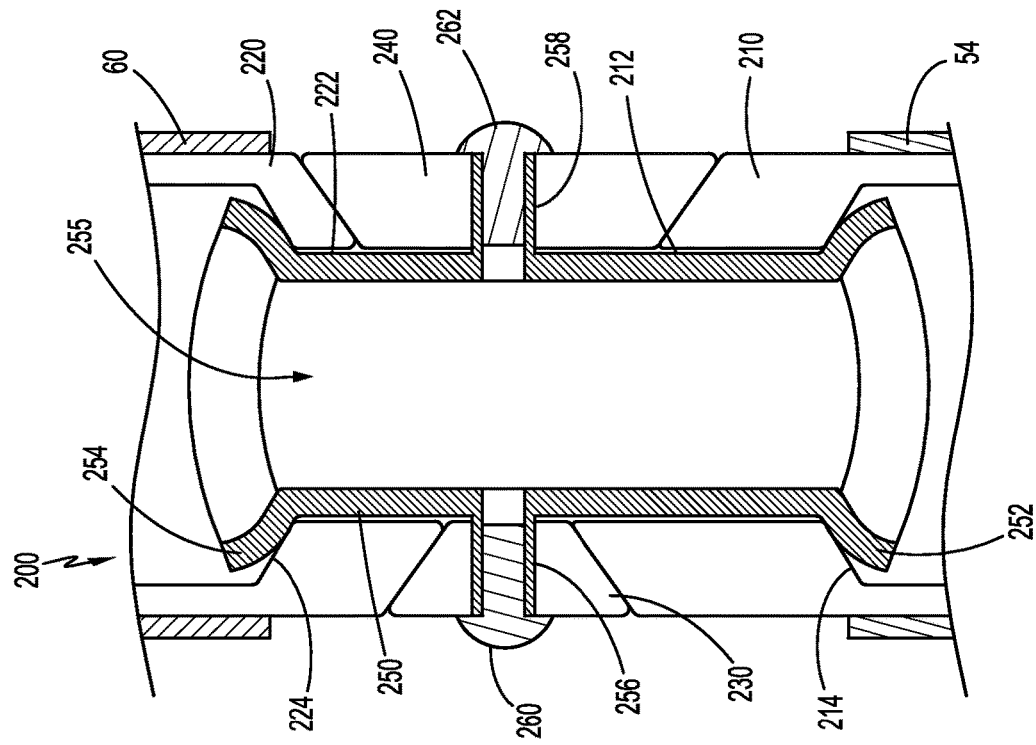
FIG. 9 is a cross-sectional view of the portion of the surgical instrument including the second type of articulation mechanism taken along section line 9-9 in FIG. 7.
Figure 8:
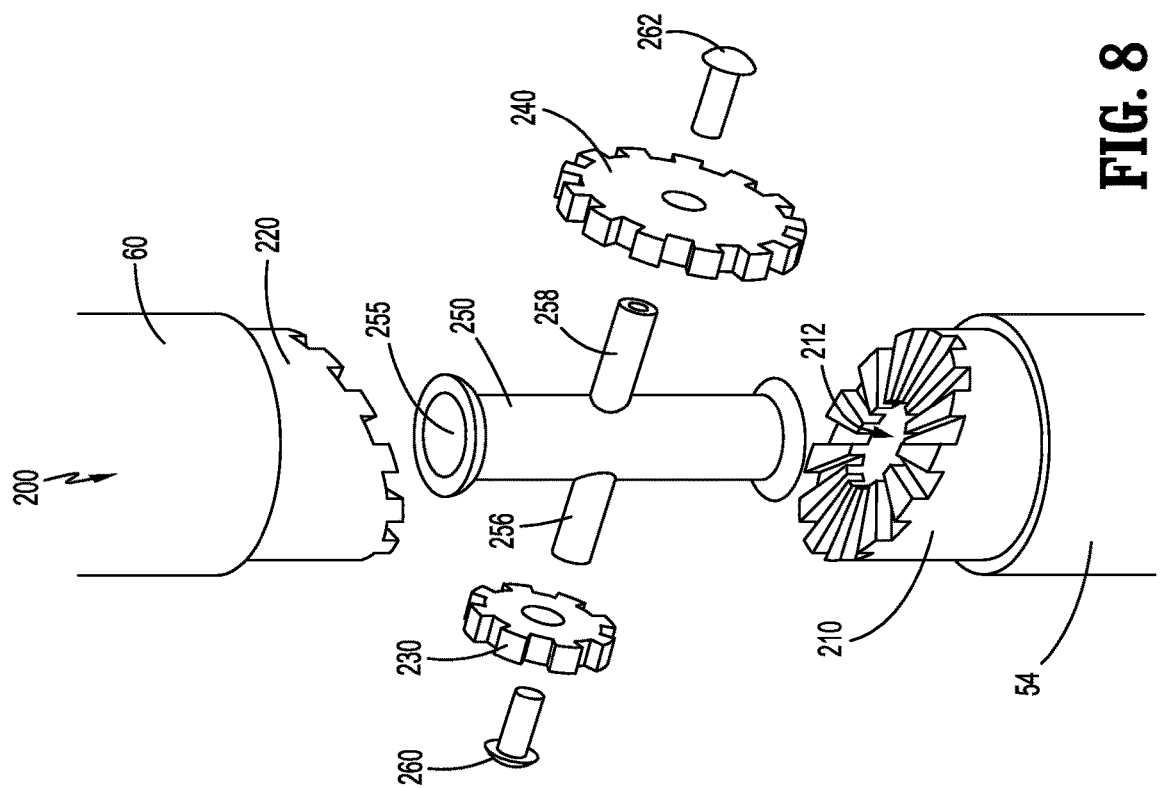
FIG. 8 is a perspective, assembly view of the portion of the surgical instrument including the second type of articulation mechanism of FIG. 7.
Figures 10, 11:
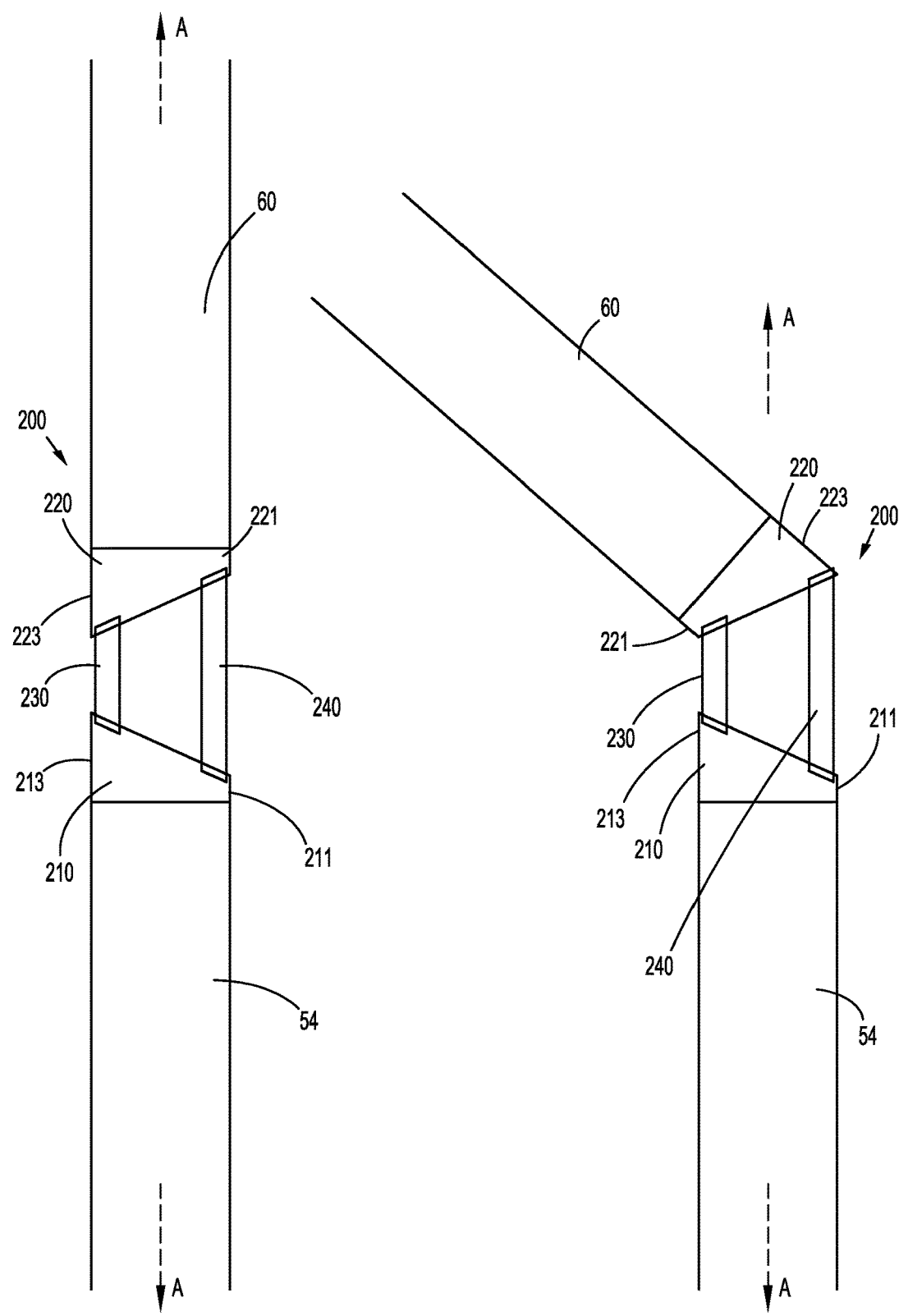
FIG. 10 is a schematic, side cross-sectional view of a portion of the surgical instrument including the second type of articulation mechanism of FIGS. 7-9, and shown in a non-articulated orientation.
FIG. 11 is a schematic, side cross-sectional view of the portion of the surgical instrument shown in FIGS. 7-9, and shown in an articulated orientation.

With specific reference to FIGS. 8 and 9, a tube 250 extends through a central aperture 212 of the proximal gear 210 and through a central aperture 222 of the distal gear 220, thereby interconnecting the distal end 55 of the shaft 54 and the end effector 60. The tube 250 includes a first flared portion 252 at its proximal end, and a second flared portion 254 at its distal end. With particular reference to FIG. 9, flared portions 252 and 254 are configured to engage respective angled portions 214 and 224 of proximal gear 210 and distal gear 220 to allow or facilitate rotation movement therebetween, while limiting longitudinal movement therebetween. Additionally, the tube 250 defines a channel 255 therethrough, which is configured to allow control mechanisms (e.g., rods, wires, sleds, etc.) to pass between the shaft 54 and the end effector 60 (e.g., to control various features of the surgical instrument 50 such as approximating jaw members, ejecting fasteners, translating a knife, etc.).

With continued reference to FIGS. 8 and 9, the tube 250 includes a first lateral projection 256 and a second lateral projection 258. The first lateral gear 230 is rotatably supported on the first lateral projection 256 and is held in place by a first pin 260 which fictionally engages the first lateral projection 256. The second lateral gear 240 is rotatably supported on the second lateral projection 258 and is held in place by a second pin 262 which frictionally engages the second lateral projection 258. The engagement between the first lateral gear 230, the first lateral projection 256, and the first pin 260 enables the first lateral gear 230 to rotate relative to the tube 250. The engagement between the second lateral gear 240, the second lateral projection 258, and the second pin 262 enables the second lateral gear 240 to rotate relative to the tube 250.

Additionally, a sheath may extend between the distal end 55 of the shaft 54 and the end effector 60 protecting each of the components of the second articulation mechanism 200 from debris during use, for instance.

In use, at least one gear is manipulated to cause a desired articulation of the end effector 60. For instance, and with particular reference to FIGS. 10 and 11, rotation of the proximal gear 210 relative to shaft 54 results in a corresponding rotation of the first lateral gear 230 and the second lateral gear 240 due to the engagement of the teeth of the respective gears. Further, the rotation of the first lateral gear 230 and the second lateral gear 240 causes a corresponding rotation of the distal gear 220 due to the engagement of the teeth of the respective gears. Due to the non-rotatable coupling between the distal gear 220 and the end effector 60, the rotation of the distal gear 220 causes the end effector 60 to move or articulate from its first position (FIG. 10) where the end effector 60 is aligned or substantially aligned with the longitudinal axis "A-A"," and its second position (FIG. 11) where the end effector 60 is off-set from the longitudinal axis "A-A."

Further, in its first position (FIG. 10), a narrow portion 211 of the proximal gear 210 is longitudinally aligned with a narrow portion 221 of the distal gear 220, and a wide portion 213 of the proximal gear 210 is longitudinally aligned with a wide portion 223 of the distal gear 220. In its second position (FIG. 11), the narrow portion 211 of the proximal gear 210 is longitudinally aligned with the wide portion 223 of the distal gear 220, and the wide portion 213 of the proximal gear 210 is longitudinally aligned with the narrow portion 221 of the distal gear 210.

Additionally, the surgical instrument 50 including the second articulation mechanism 200 has improved access to target tissue by having the ability to rotate. That is, the proximal portion 56 of the shaft 54 of the surgical instrument 50 can rotate about itself (e.g., the longitudinal axis "A-A"), thereby causing the end effector 60 (either in an articulated position or a non-articulated position) to rotate about the longitudinal axis "A-A."

Figure 12:
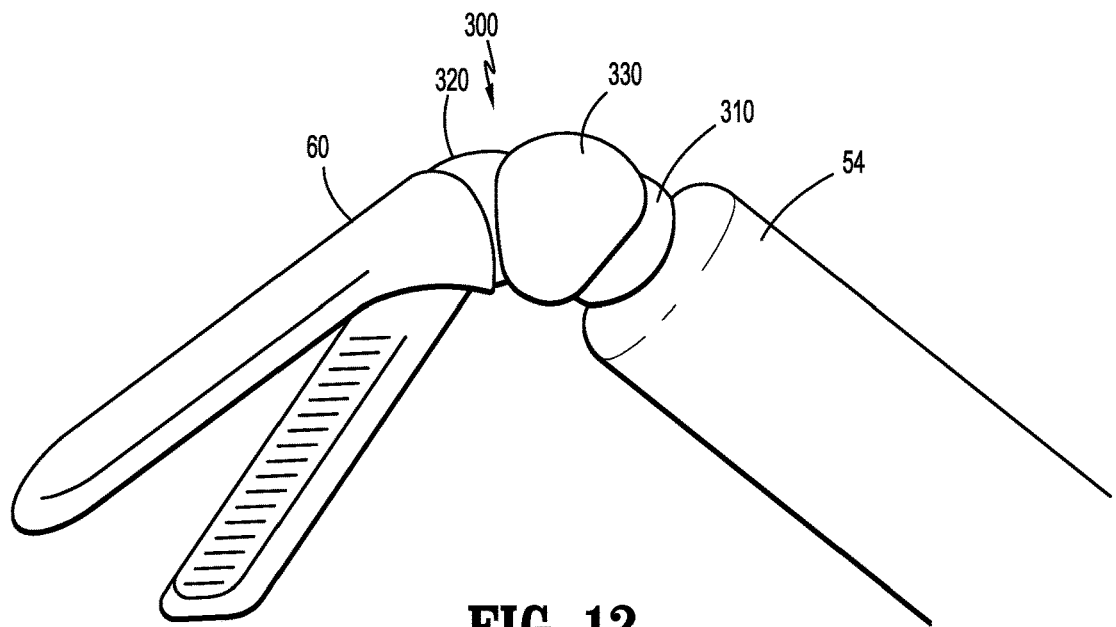
FIG. 12 is a perspective view of a distal portion of a surgical instrument including a third type of articulation mechanism.
Figure 13:
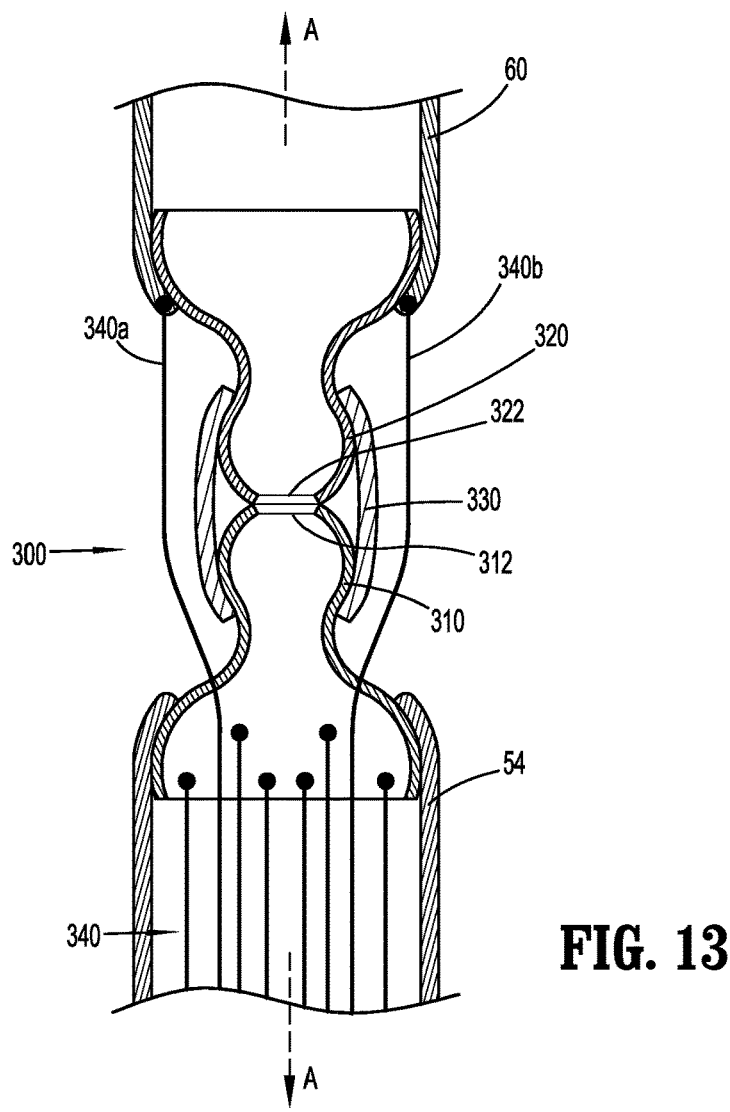
FIG. 13 is a cross-sectional view of a distal portion of the surgical instrument of FIG. 12 including the third type of articulation mechanism and shown in a non-articulated orientation.
Figure 14:
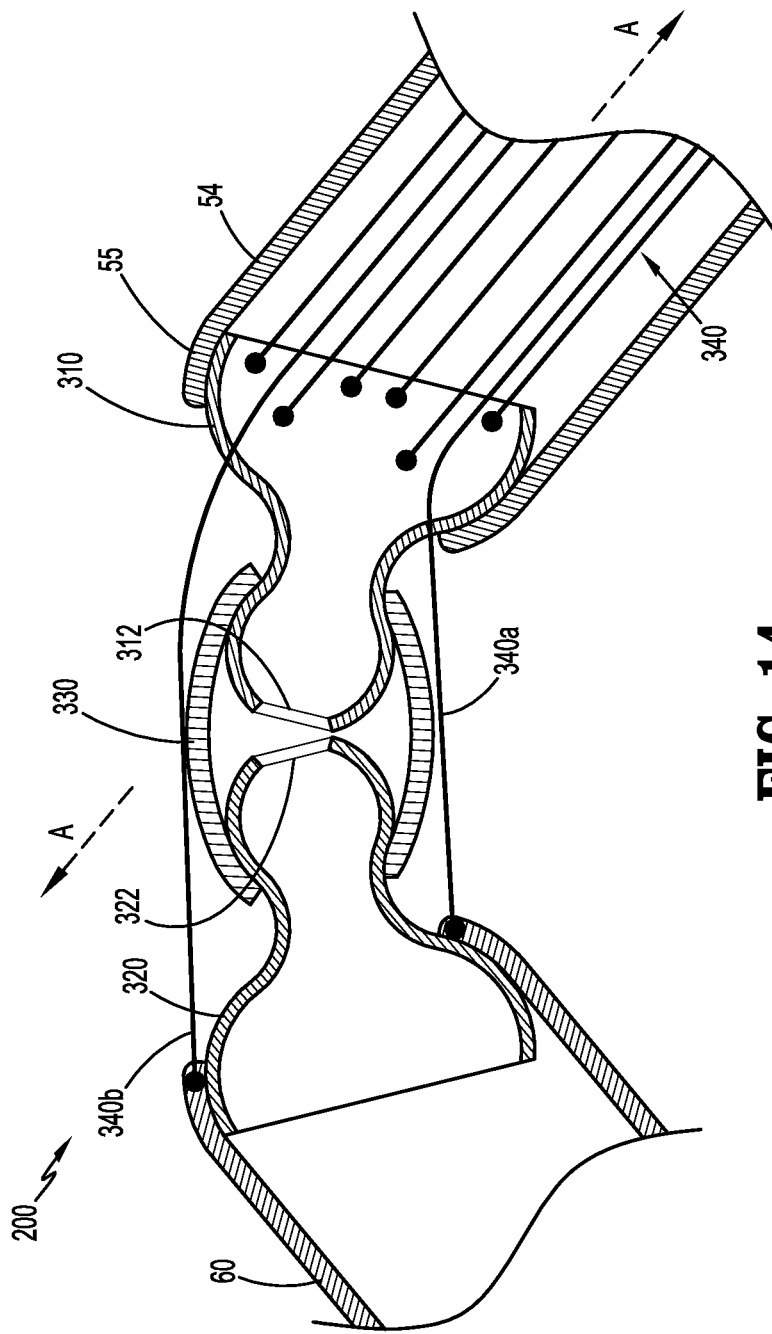
FIG. 14 is a cross-sectional view of a distal portion of the surgical instrument of FIG. 12 including the third type of articulation mechanism and shown in an articulated orientation.

With reference to FIGS. 12-14, a third embodiment of an articulation mechanism is shown and is generally indicated by reference character 300. Articulation mechanism 300 is disposed at or near the distal end 55 of the shaft 54 of the surgical instrument 50, and is mechanically coupled to the end effector 60. The articulation mechanism 300 is configured to allow the end effector 60 to move relative to the proximal portion 56 of the shaft 54 to help improve the versatility of the surgical instrument 50, for example. The articulation mechanism 300 includes a proximal ball joint 310, a distal ball joint 320, a cuff 330, and a plurality of cables 340. The cuff 330 (e.g., an encapsulating cuff) interconnects the proximal ball joint 310 and the distal ball joint 320. Any or all cables of the plurality of cables 340 may be sufficiently rigid such that movement (e.g., longitudinal, rotational, etc.) of the proximal end directly corresponds to movement at the distal end, and simultaneously, may be sufficiently bendable to bend around an articulation joint (FIG. 14).

The proximal ball joint 310 is rotatably engaged with the distal end 55 of the shaft 54, and the distal ball joint 320 is rotatably engaged with a proximal end of the end effector 60. Additionally, the proximal ball joint 310 and the distal ball joint 320 each define a respective channel 312, 322 therethrough, which together form a path that is configured to allow control mechanisms (e.g., rods, wires, sleds, etc.) to pass between the shaft 54 and the end effector 60 (e.g., to control various features of the surgical instrument 50 such as approximating jaw members, ejecting fasteners, translating a knife, etc.).

Some cables of the plurality of cables 340 (e.g., a first cable 340a and a second cable 340b) are affixed to or otherwise engaged with a proximal end of the end effector 60, and other cables of the plurality of cables 340 are affixed to or otherwise engaged with the proximal ball joint 310. Additionally, the cuff 330 is non-rotatably coupled to the proximal ball joint 310 and to the distal ball joint 320. Thus, the cuff 300 helps transfer the movement of the proximal ball joint 310 to the distal ball joint 320.

Further, a sheath may extend between the distal end 55 of the shaft 54 and the end effector 60 protecting each of the components of the third articulation mechanism 300 from debris during use, for instance.

In use, the plurality of cables 340 is manipulated (e.g., by the surgical robot, adapter, etc.) to cause a desired articulation of the end effector 60. For instance, and with particular reference to FIG. 14, proximal movement of the first cable 340a in connection with distal movement of the second cable 340b causes the end effector 60 to move from its first position (FIG. 13) where the end effector 60 is aligned or substantially aligned with the longitudinal axis "A-A"," to its second position (FIG. 14) where the end effector 60 is off-set from the longitudinal axis "A-A." Additionally, movement of the plurality of cables 340 that are engaged with the proximal ball joint 310 can cause relatively slight movements of the proximal ball joint relative to the shaft 54 thereby enabling more precise control of the distal ball joint 320 and the end effector 60 engaged therewith.

Further, the surgical instrument 50 including the third articulation mechanism 300 has improved access to target tissue by having the ability to rotate. That is, the proximal portion 56 of the shaft 54 of the surgical instrument 50 can rotate about itself (e.g., the longitudinal axis "A-A"), thereby causing the end effector 60 (either in an articulated position or a non-articulated position) to rotate about the longitudinal axis "A-A."

Figure 15:
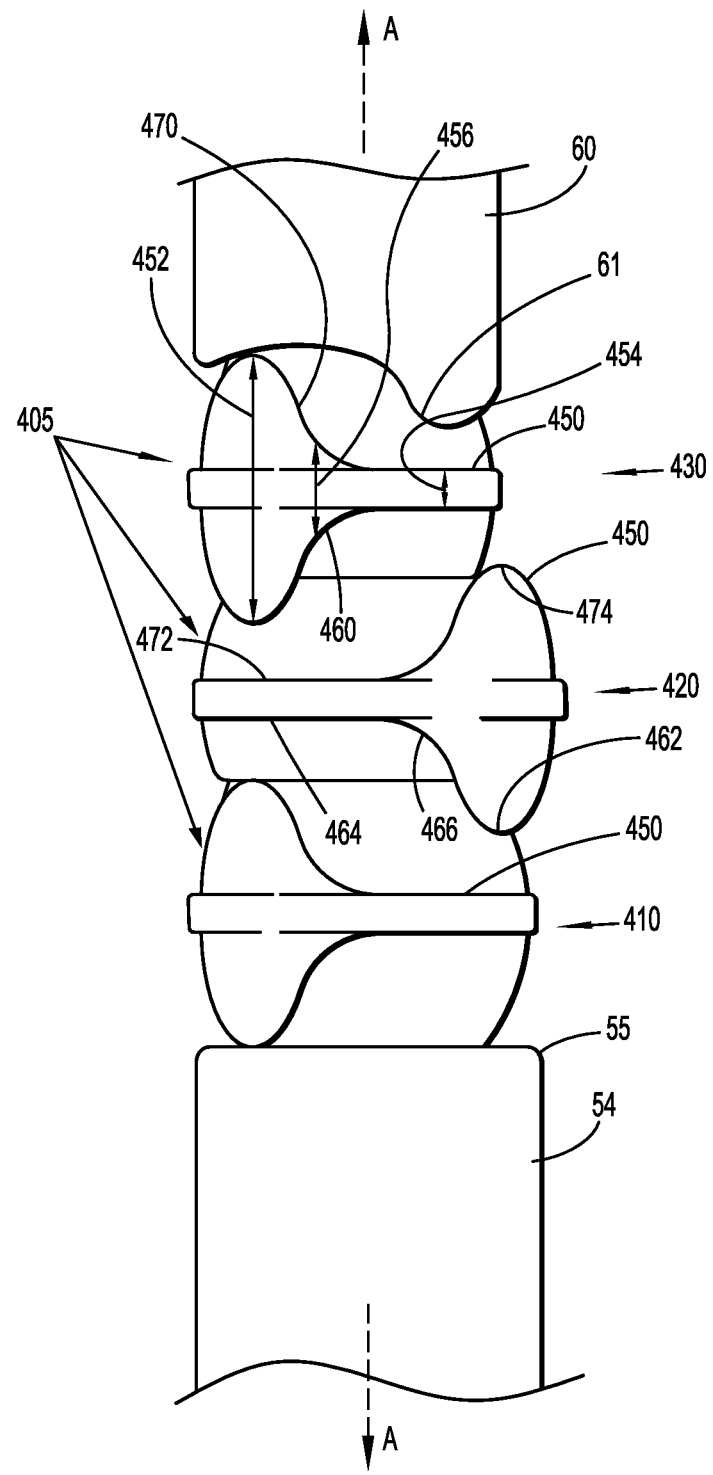
FIG. 15 is a side view of a fourth type of articulation mechanism for use with a surgical instrument and shown in a non-articulated orientation.
Figure 16:
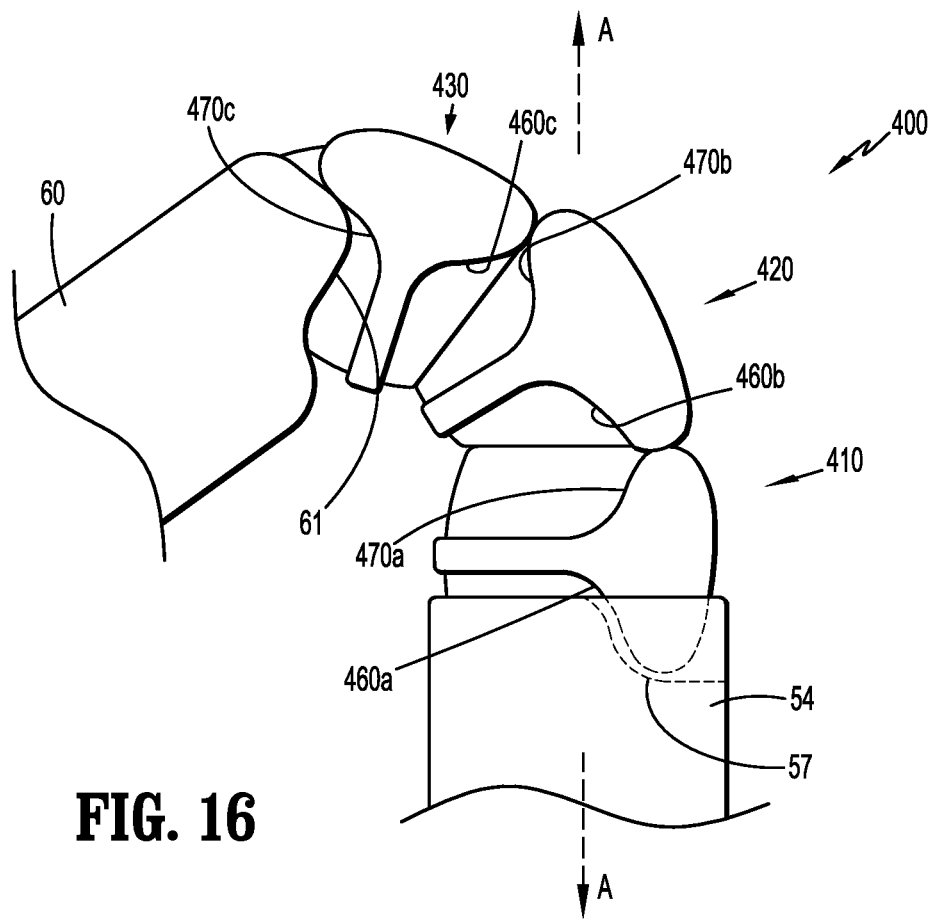
FIG. 16 is a side view of the fourth type of articulation mechanism shown in FIG. 15 and shown in an articulated orientation.
Figure 17:
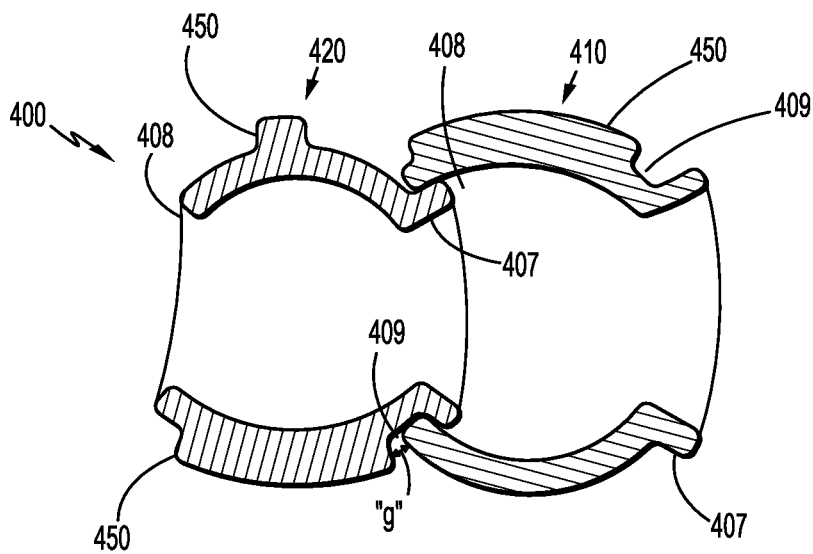
FIG. 17 is a cross-sectional view of a pair of linkages of the fourth type of articulation mechanism of FIGS. 15 and 16.

With reference to FIGS. 15-17, a fourth embodiment of an articulation mechanism is shown and is generally indicated by reference character 400. Articulation mechanism 400 is disposed between the shaft 54 and the end effector 60 (or disposed between two portions of the shaft 54). The articulation mechanism 400 is configured to allow the end effector 60 to move relative to the proximal portion 56 of the shaft 54 to help improve the versatility of the surgical instrument 50, for example. The articulation mechanism 400 includes a plurality of ball joints 405. While the illustrated embodiment shows the plurality of ball joints 405 including three ball joints—a first ball joint 410, a second ball joint 420, and a third ball joint 430—the plurality of ball joints 405 may include more or fewer than three ball joints.

The first ball joint 410 rotatably engaged with the distal end 55 of the shaft 54, and the third ball joint 430 is rotatably engaged with the proximal end of the end effector 60. The second ball joint 420 is rotatably engaged with both the first ball joint 410 and the third ball joint 430. Additionally, and with particular reference to FIG. 17, the first ball joint 410 and the second ball joint 420 each define a respective channel 412, 422 therethrough, which together with a channel extending through the third ball joint 430 (not shown in FIG. 17) form a path that is configured to allow control mechanisms (e.g., rods, wires, sleds, etc.) to pass between the shaft 54 and the end effector 60 (e.g., to control various features of the surgical instrument 50 such as approximating jaw members, ejecting fasteners, translating a knife, etc.).

Each of the plurality of ball joints 405 includes a camming surface 450 on an external surface thereof, which is configured to engaged a corresponding camming surface 450 of an adjacent ball joint and/or a camming surface 57 (FIG. 16) of the shaft 54 and/or a camming surface 61 of the end effector 60. Additionally, while the illustrated embodiments show each of the first ball joint 410, the second ball joint 420 and the third ball joint 430 being identical or substantially identical, it is envisioned and within the scope of the present disclosure that at least one ball joint includes a different camming surface than the other ball joints, for instance.

The camming surface 450 or ledge of each ball joint includes a proximal camming surface 460 and a distal camming surface 470. A proximal camming surface 460a of the first ball joint 410 rotatably engages the camming surface 57 of the shaft 54 (e.g., within an outer wall of the shaft 54). A distal camming surface 470a of the first ball joint 410 rotatably engages a proximal camming surface 460b of the second ball joint 420. A distal camming surface 470b of the second ball joint 420 rotatably engages a proximal camming surface 460c of the third ball joint 430. A distal camming surface 470c of the third ball joint 430 rotatably engages the camming surface 61 of the end effector 60.

With particular reference to FIG. 15, the camming surface 450 generally defines a wide portion 452, a narrow portion 454, and a curved portion 456 interconnecting the wide portion 452 and the narrow portion 454. More particularly, the proximal camming surface 460 of the ball joints defines a proximal portion 462, a distal portion 464 and a curved portion 466 interconnecting the proximal portion 462 and the distal portion 464. The distal camming surface 470 defines a proximal portion 472, a distal portion 474 and a curved portion 476 interconnecting the proximal portion 472 and the distal portion 474. The wide portion 452 of the camming surface 450 is defined between the proximal portion 462 of the proximal camming surface 460 and the distal portion 474 of the distal camming surface 470. The narrow portion 454 of the camming surface 450 is defined between the distal portion 464 of the proximal camming surface 460 and the proximal portion 472 of the distal camming surface 470. The curved portion 456 of the camming surface 450 is defined between the curved portion 466 of the proximal camming surface 460 and the curved portion 476 of the distal camming surface 470.

The camming surfaces 450 of the plurality of ball joints 405 are designed such that rotation of one ball joint or the shaft 54 causes rotation and/or off-axis tilting of another ball joint and/or of the end effector 60, for example. More particularly, as the first ball joint 410 is rotated a sufficient amount about the longitudinal axis "A-A" (either independently rotated or in response to rotation of the shaft 54), the distal camming surface 470 of the first ball joint 410 engages the proximal camming surface 460 of the second ball joint 420. Even more particularly, a predetermined amount of rotation of the first ball joint 410 causes the curved portion 476 and the distal portion 474 of the distal camming surface 470 of the first ball joint 410 to contact the curved portion 466 and the proximal portion 462 of the proximal camming surface 460 of the second ball joint 420. This engagement causes the second ball joint 420 to move, pivot, tilt or cam away from the first ball joint 410. Maximum movement, pivoting, titling or camming of the second ball joint 420 relative to the first ball joint 410 occurs when the distal portion 474 of the distal camming surface 470 of the first ball joint 410 contacts the proximal portion 462 of the proximal camming surface 460 of the second ball joint 420.

It is envisioned that, in this position, the first ball joint 410 becomes releasably locked with the second ball joint 420, such that continued rotation of the first ball joint 410 causes both first ball joint 410 and second ball joint 420 to rotate. This releasable locking engagement may be accomplished by the second ball joint 420 bottoming out relative to the first ball joint 410 such that additional movement, pivoting, tilting or camming is physically prevented due to the geometry of the ball joints 410, 420. It is also envisioned that magnets disposed on selective portions of the first ball joint 410 and the second ball joint 420, for instance, can releasably lock first ball joint 410 and second ball joint 420. Further, a finger extending from at least one of the first ball joint 410 or the second ball joint 410, toward the other, may limit the amount the first ball joint 410 can rotate relative to the second ball joint 420 in a particular direction. In these configurations, continued rotation of the first ball joint 410 results in a corresponding rotation of the second ball joint 420. It is further envisioned that the releasable locking engagement, the finger, or similar structures, are also utilized for the engagement between other adjacent ball joints of the plurality of ball joints 405 and/or the shaft 54 and/or the end effector 60.

With particular reference to FIG. 16, rotation of the second ball joint 420 relative to the third ball joint 430 causes the third ball joint 430 to move, pivot, tilt or cam away from the second ball joint 420, in the same manner as described above with regard to the movement of the second ball joint 420 relative to the first ball joint 410. Maximum movement, pivoting, titling or camming of the third ball joint 430 relative to the second ball joint 420 likewise occurs when the distal portion 474 of the distal camming surface 470 of the second ball joint 420 contacts the proximal portion 462 of the proximal camming surface 460 of the third ball joint 430. Additionally, due the engagement between the distal camming surface 470 of the third ball joint 430 and the camming surface 61 of the end effector 60, rotation of the third ball joint 430 relative to the end effector 60 causes the end effector 60 to move, pivot, tilt or cam away from the third ball joint 430.

Referring now to FIG. 17, the engagement between adjacent ball joints is shown. That is, a proximal end 407 of each ball joint 405 is flared and is positioned within a distal opening 408 of a proximally-adjacent ball joint 405. For example, in FIG. 17, the flared proximal end 407 of the second ball joint 420 is positioned within the distal opening 408 of the first ball joint 410. Additionally, the flared proximal end 407 of the first ball joint 410 is positionable within a distal opening of the shaft 54. Similarly, while not explicitly shown in FIG. 17, the third ball joint 430 engages the second ball joint 420, and engages a proximal end of the end effector 60 in the same or a similar manner.

FIG. 17 also illustrates a proximal slot 409 defined in each ball joint 405. As shown, the proximal slot 409 (of the second ball joint 420) is wider than the thickness of the adjacent ball joint (the first ball joint 410; not including the camming surface 450). The difference between the width of the proximal slot 409 and the thickness of the ball joint 405 is defined as a gap "g." The gap "g" helps allow and determine the extent of the movement, pivoting, tilting or camming of one ball joint relative to an adjacent ball joint.

Further, a sheath may extend between the distal end 55 of the shaft 54 and the end effector 60 protecting each of the components of the fourth articulation mechanism 400 from debris during use, for instance.

In use, rotation of the shaft 54 and/or the first ball joint 410 is manipulated (e.g., by the surgical robot, adapter, etc.) to cause a desired articulation of the end effector 60. For instance, and with particular reference to FIGS. 15 and 16, a predetermined amount of rotation of the first ball joint 410 (e.g., in the clockwise direction) relative to the shaft 54 causes the second ball joint 420 (and thus the third ball joint 430, and the end effector 60) to move from its first position (FIG. 15) where the end effector 60 is aligned or substantially aligned with the longitudinal axis "A-A"," into a second position (an amount of articulation between FIGS. 15 and 16) where the end effector 60 is off-set from the longitudinal axis "A-A." Continued rotation of the first ball joint 410 relative to the shaft 54 results in rotation of the third ball joint 430, and continued movement of the end effector 60, as discussed above, such that the end effector 60 is in its fully articulated position (FIG. 16).

Additionally, the surgical instrument 50 including the fourth articulation mechanism 400 has improved access to target tissue by having the ability to rotate. That is, the proximal portion 56 of the shaft 54 of the surgical instrument 50 can rotate about itself (e.g., the longitudinal axis "A-A"), thereby causing the end effector 60 (either in an articulated position or a non-articulated position) to rotate about the longitudinal axis "A-A."

With reference to FIGS. 18-21, a fifth embodiment of an articulation mechanism is shown and is generally indicated by reference character 500. Articulation mechanism 500 is disposed at or near the distal end 55 of the shaft 54 of the surgical instrument 50, and is mechanically coupled to the end effector 60. The articulation mechanism 500 is configured to allow the end effector 60 to move relative to the proximal portion 56 of the shaft 54 to help improve the versatility of the surgical instrument 50, for example. The articulation mechanism 500 includes a ball joint 510 and a plurality of drivers 540. The ball joint 510 includes a ball 520 and a claw 524. The claw 524 includes a ring 526 having a plurality of fingers 530, with each finger 530 configured to rotatably engage the ball 520. While the ball 520 is shown engaged with the shaft 54, and the claw 524 is shown engaged with the end effector 60, the positions of the ball 520 and the claw 524 may be reversed without departing from the scope of the present disclosure.

Figure 21:
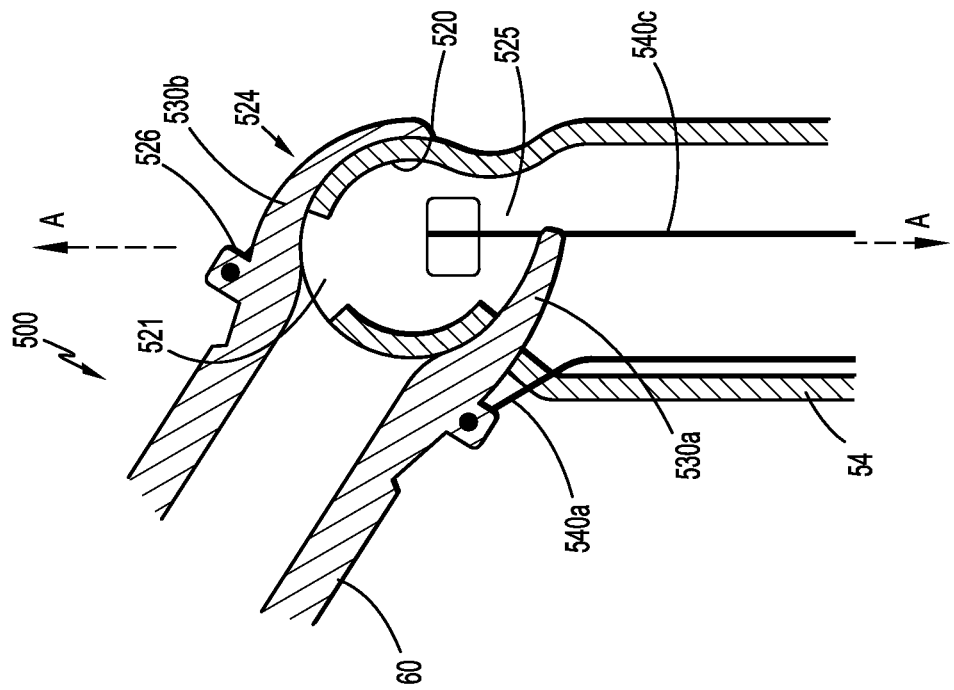
FIG. 21 is a cross-sectional view of the articulation mechanism of FIGS. 18-20 shown in an articulated orientation.

As shown in FIG. 21, the ball 520 and the claw 524 of the ball joint 510 each define a respective channel 521, 525 therethrough, which together form a path that is configured to allow control mechanisms (e.g., rods, wires, sleds, etc.) to pass between the shaft 54 and the end effector 60 (e.g., to control various features of the surgical instrument 50 such as approximating jaw members, ejecting fasteners, translating a knife, etc.).

In the illustrated embodiment, the claw 524 includes three fingers—a first finger 530a, a second finger 530b, and a third finger 530c. The claw 524 may include more or fewer than three fingers without departing from the scope of the present disclosure. The plurality of fingers 530 are equally or substantially equally radially positioned on the end effector 60 (or on a connecting structure), such that in the embodiment with three fingers 530, each finger 530 is separated from its adjacent fingers 530 by about 120°.

Each of the fingers 530 is arcuate to match or substantially match the curvature of the ball 520, and each finger 530 extends proximally from the ring 526 to rotatably engage the ball 520 of the ball joint 510. More particularly, a proximal end 532 of each finger 530 is positioned and configured to move through a corresponding aperture 523 of the ball 520. That is, the first finger 530a engages or selectively engages a first aperture 523a, the second finger 530b engages or selectively engages a second aperture 523b, and the third finger 530c engages or selectively engages a third aperture 523c.

Each finger 530a, 530b, 530c is configured to at least partially enter into or move deeper into the respective aperture 523a, 523b, 523c during articulation of the end effector 60 in a particular direction. More particularly, for example, when the end effector 60 is articulated toward the first finger 530a, at least a portion of the first finger 530a enters or moves deeper into the first aperture 523a (while the second finger 530b and the third finger 530b move away from respective apertures 523b, 523c).

Figure 19:
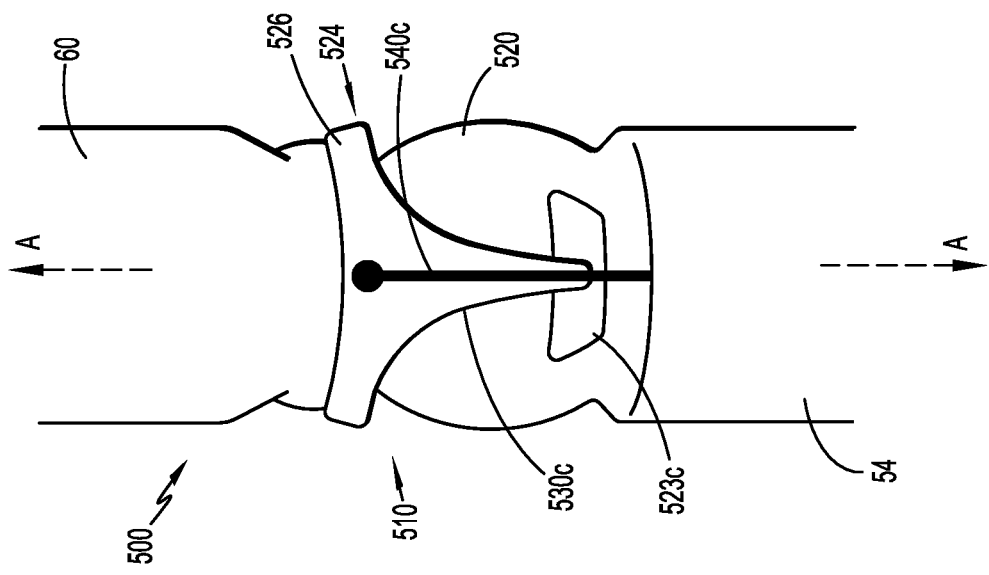
FIG. 19 is a second, side view of the fifth type of articulation mechanism of FIG. 18 and shown in a non-articulated orientation, and where the second, side view is offset 180° from the first, side view of FIG. 18.
Figure 18:
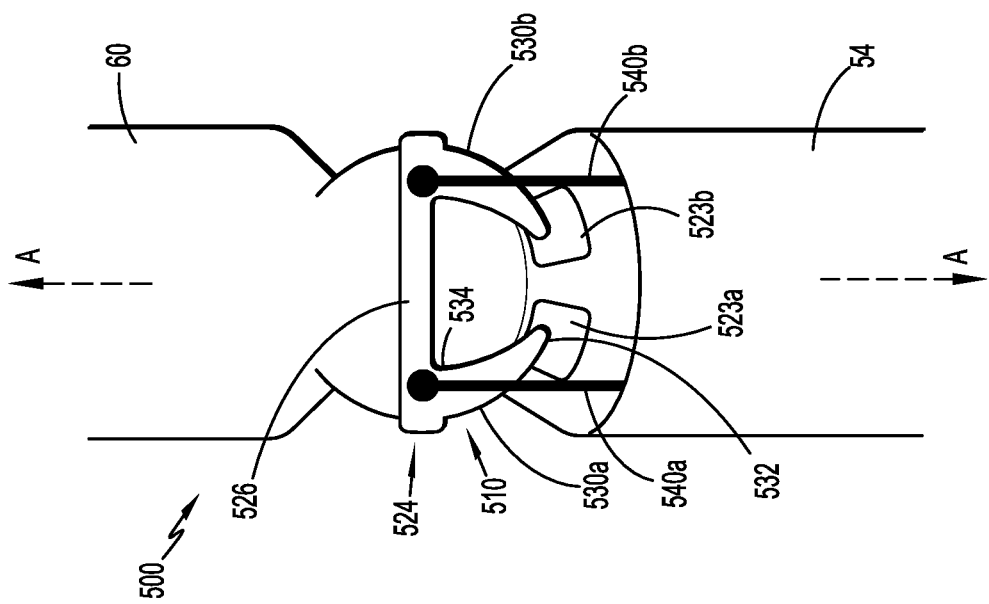
FIG. 18 is a first, side view of a fifth type of articulation mechanism for use with a surgical instrument and shown in a non-articulated orientation.
Figure 20:
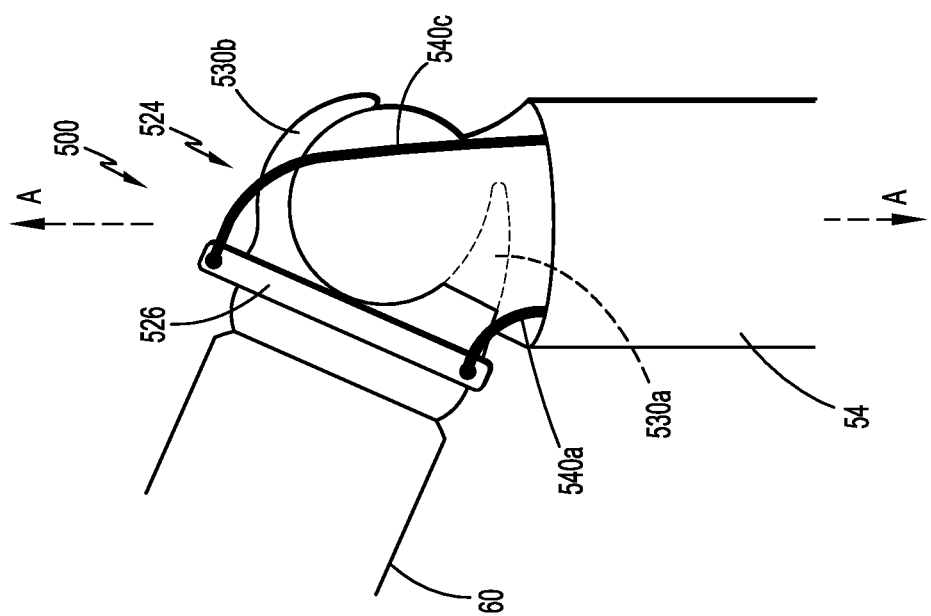
FIG. 20 is a side view of the fifth type of articulation mechanism of FIG. 18 shown in an articulated orientation.

Referring to FIGS. 18-20, the plurality of drivers 540 includes three drivers—a first driver 540a, a second driver 540b, and a third driver 540c. The articulation mechanism 500 may include more or fewer than three drivers without departing from the scope of the present disclosure. Additionally, the articulation mechanism 500 may have an equal amount of fingers 530 and drivers 540 (as shown), may include more fingers 530 than drivers 540, or may include fewer fingers 530 than drivers 540. In the illustrated embodiment, each driver 540 is radially aligned or substantially radially aligned with a corresponding finger 530, such that each driver 540 is separated from its adjacent drivers 540 by about 120°. The drivers 540 can be attached to the end effector 60 at a variety of positions, including a proximal end of the end effector 60, a distal end 534 of a respective finger 530, or the ring 526 of the claw 524, for instance.

Any or all drivers of the plurality of drivers 540 may be sufficiently rigid such that movement (e.g., longitudinal, rotational, etc.) of the proximal end directly corresponds to movement at the distal end, and simultaneously, may be sufficiently bendable to bend around an articulation joint (FIG. 20).

Further, a sheath may extend between the distal end 55 of the shaft 54 and the end effector 60 protecting each of the components of the fifth articulation mechanism 500 from debris during use, for instance.

In use, the plurality of drivers 540 is manipulated (e.g., by the surgical robot, adapter, etc.) to cause a desired articulation of the end effector 60. For instance, and with particular reference to FIGS. 20 and 21, proximal movement of the first driver 540a in connection with distal movement of the second driver 540b and distal movement of the third driver 540c (hidden from view in FIG. 21) causes the end effector 60 to move from its first position (FIGS. 19 and 20) where the end effector 60 is aligned or substantially aligned with the longitudinal axis "A-A"," to its second position (FIGS. 20 and 21) where the end effector 60 is off-set from the longitudinal axis "A-A." Additionally, as noted above, proximal movement of the first driver 540a causes at least a portion of the first finger 530a to enter or move deeper into the first aperture 523a (while the second finger 530b and the third finger 530b move away from respective apertures 523b, 523c). Further, moving any combination of one driver proximally and/or two drivers distally (any vice versa) relative to the shaft 54 enables a wide or complete range of positioning the end effector 60.

Additionally, the surgical instrument 50 including the fifth articulation mechanism 500 has improved access to target tissue by having the ability to rotate. That is, the proximal portion 56 of the shaft 54 of the surgical instrument 50 can rotate about itself (e.g., the longitudinal axis "A-A"), thereby causing the end effector 60 (either in an articulated position or a non-articulated position) to rotate about the longitudinal axis "A-A."

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

The invention claimed is:

1. A surgical instrument, comprising:
   a shaft defining a longitudinal axis;
   an effector disposed adjacent a distal end of the shaft and defining a respective longitudinal axis; and
   an articulation mechanism disposed in mechanical cooperation with the shaft and the end effector, the articulation mechanism configured to allow the end effector to move between a first position where at least a portion of the end effector defining the longitudinal axis thereof is aligned with the longitudinal axis and a second position where the portion of the end effector defining the longitudinal axis thereof is disposed at an angle relative to the longitudinal axis of the shaft, the articulation mechanism including:
   a proximal gear disposed in mechanical cooperation with the shaft;
   a distal gear disposed in mechanical cooperation with the end effector;
   a first lateral gear disposed in contact with the proximal gear and the distal gear; and
   a second lateral gear disposed in contact with the proximal gear and the distal gear, wherein the first lateral gear has a smaller diameter than the second lateral gear.

2. The surgical instrument according to claim 1, wherein the first lateral gear is disposed on a first lateral side of the longitudinal axis of the shaft, and the second lateral gear is disposed on a second lateral side of the longitudinal axis of the shaft.

3. The surgical instrument according to claim 1, wherein the proximal gear is a bevel gear.

4. The surgical instrument according to claim 3, wherein the distal gear is a bevel gear.

5. The surgical instrument according to claim 4, wherein the first lateral gear has a smaller diameter than the second lateral gear, wherein the first lateral gear is a bevel gear, and wherein the second lateral gear is a bevel gear.

6. The surgical instrument according to claim 4, wherein when the end effector is in the first position, a narrow portion of the proximal gear is longitudinally aligned with a narrow portion of the distal gear, and a wide portion of the proximal gear is longitudinally aligned with a wide portion of the distal gear.

7. The surgical instrument according to claim 6, wherein when the end effector is in the second position, the narrow portion of the proximal gear is longitudinally aligned with the wide portion of the distal gear, and the wide portion of the proximal gear is longitudinally aligned with the narrow portion of the distal gear.

8. The surgical instrument according to claim 1, wherein the proximal gear of the surgical instrument is configured to be rotated by a robot.

9. A surgical instrument, comprising:
   a shaft defining a longitudinal axis;
   an effector disposed adjacent a distal end of the shaft and defining a respective longitudinal axis;
   an articulation mechanism disposed in mechanical cooperation with the shaft and the end effector, the articulation mechanism configured to allow the end effector to move between a first position where at least a portion of the end effector defining the longitudinal axis thereof is aligned with the longitudinal axis and a second position where the portion of the end effector defining the longitudinal axis thereof is disposed at an angle relative to the longitudinal axis of the shaft, the articulation mechanism including:
   a proximal gear disposed in mechanical cooperation with the shaft;
   a distal gear disposed in mechanical cooperation with the end effector;
   a first lateral gear disposed in contact with the proximal gear and the distal gear; and
   a second lateral gear disposed in contact with the proximal gear and the distal gear; and
   a tube extending through a central aperture of the proximal gear and through a central aperture of the distal gear.

10. The surgical instrument according to claim 9, wherein a proximal end of the tube includes a flared portion configured to engage an angled portion of the proximal gear.

11. The surgical instrument according to claim 10, wherein a distal end of the tube includes a flared portion configured to engage an angled portion of the distal gear.

12. The surgical instrument according to claim 9, wherein the tube includes a first lateral projection for rotatably supporting the first lateral gear, and a second lateral projection for rotatably supporting the second lateral gear.

13. The surgical instrument according to claim 12, wherein the first lateral projection and the second lateral projection extend from the same longitudinal position of the tube.

14. An articulation mechanism for use with a surgical instrument, the articulation mechanism comprising:
- a proximal bevel gear disposed in mechanical cooperation with a shaft of the surgical instrument;
- a distal bevel gear disposed in mechanical cooperation with an end effector of the surgical instrument;
- a first lateral gear disposed in contact with the proximal bevel gear and the distal bevel gear; and
- a second lateral gear disposed in contact with the proximal bevel gear and the distal bevel gear, wherein the first lateral gear has a smaller diameter than the second lateral gear.

15. The articulation mechanism according to claim 14, wherein the first lateral gear is a bevel gear, wherein the second lateral gear is a bevel gear, and wherein the first lateral gear is free from contact with the second lateral gear.

16. The articulation mechanism according to claim 15, further comprising a tube extending through a central aperture of the proximal gear and through a central aperture of the distal gear, the tube configured to prevent longitudinal movement of the distal bevel gear relative to the proximal bevel gear.

17. The articulation mechanism according to claim 16, wherein a proximal end of the tube includes a flared portion configured to rotatably engage an angled portion of the proximal gear, and a distal end of the tube includes a flared portion configured to rotatably engage an angled portion of the distal gear.

18. The articulation mechanism according to claim 17, wherein the tube includes a first lateral projection for rotatably supporting the first lateral gear, and a second lateral projection for rotatably supporting the second lateral gear.

19. The articulation mechanism according to claim 18, wherein the first lateral projection and the second lateral projection extend from the same longitudinal position of the tube.

* * * * *